United States Patent [19]
Alesi, Jr.

[11] Patent Number: 5,462,542
[45] Date of Patent: Oct. 31, 1995

[54] STERNUM BUCKLE WITH SERRATED STRAP

[75] Inventor: Thomas W. Alesi, Jr., New Fairfield, Conn.

[73] Assignee: United States Surgical Corporation, Norwalk, Conn.

[21] Appl. No.: 186,409

[22] Filed: Jan. 24, 1994

[51] Int. Cl.⁶ .................................................. A61B 17/04
[52] U.S. Cl. .......................... 606/151; 606/216; 24/16 R; 24/17 AP
[58] Field of Search ...................................... 606/213, 215, 606/228, 216, 151; 24/16 R, 17 AP

[56] References Cited

U.S. PATENT DOCUMENTS

| | | |
|---|---|---|
| 3,570,497 | 3/1971 | Lemole . |
| 3,577,601 | 5/1971 | Mariani . |
| 3,802,438 | 4/1974 | Wolvek . |
| 3,822,818 | 7/1974 | Strekopytov et al. . |
| 3,926,193 | 12/1975 | Hasson . |
| 4,009,509 | 3/1977 | McCormick . |
| 4,037,603 | 7/1977 | Wendorff . |
| 4,078,559 | 3/1978 | Nissinen . |
| 4,119,091 | 10/1978 | Partridge . |
| 4,122,989 | 10/1978 | Kapitanov et al. . |
| 4,135,749 | 1/1979 | Caveney et al. . |
| 4,138,770 | 2/1979 | Barrette et al. . |
| 4,146,022 | 3/1979 | Johnson et al. . |
| 4,183,119 | 1/1980 | Stewart et al. . |
| 4,201,215 | 5/1980 | Crossett et al. . |
| 4,210,148 | 7/1980 | Stivala . |
| 4,236,280 | 12/1980 | Kreiseder . |
| 4,269,180 | 5/1981 | Dall et al. . |
| 4,279,248 | 7/1981 | Gabbay . |
| 4,287,644 | 9/1981 | Durand . |
| 4,413,380 | 11/1983 | Suzuki . |
| 4,473,524 | 9/1984 | Paradis . |
| 4,512,346 | 4/1985 | Lemole . |
| 4,532,679 | 8/1985 | Scott . |
| 4,535,764 | 8/1985 | Ebert . |
| 4,537,432 | 8/1985 | Meeks . |
| 4,580,319 | 4/1986 | Paradis . |
| 4,583,541 | 4/1986 | Barry . |
| 4,658,478 | 4/1987 | Paradis . |
| 4,730,615 | 3/1988 | Sutherland et al. . |
| 4,754,529 | 7/1988 | Paradis . |
| 4,802,477 | 2/1989 | Gabbay . |
| 4,813,416 | 3/1989 | Pollak et al. . |
| 4,896,668 | 1/1990 | Popoff et al. . |
| 4,944,753 | 7/1990 | Burgess et al. . |
| 4,950,284 | 8/1990 | Green et al. . |
| 4,950,285 | 8/1990 | Wilk . |
| 4,955,913 | 9/1990 | Robinson . |
| 4,966,600 | 10/1990 | Songer et al. . |
| 5,031,943 | 7/1991 | Scott et al. . |
| 5,053,047 | 10/1991 | Yoon . |
| 5,123,686 | 6/1992 | Wenk . |
| 5,123,913 | 6/1992 | Wilk et al. . |
| 5,139,498 | 8/1992 | Ley . |
| 5,146,654 | 9/1992 | Caveney et al. . |
| 5,163,598 | 11/1992 | Peters et al. . |
| 5,196,022 | 3/1993 | Bilweis . |

*Primary Examiner*—Gary Jackson

[57] ABSTRACT

A strap assembly to be looped about split portions of tissue includes a flexible elongated strap and a buckle member attached to one end portion of the elongated strap. The strap includes a plurality of ratchet teeth along a portion thereof. The buckle member includes a base member defining a generally transverse channel dimensioned for reception of the elongated strap and a pawl member pivotally connected to the base member. The pawl member includes pawl teeth complementary in dimension and configuration to the ratchet teeth of the elongated strap. The pawl teeth interlockingly engage the ratchet teeth to secure the elongated strap in a looped tensioned condition about the tissue. The strap and buckle are preferably integrally formed of a bioabsorbable material. The assembly has particular application in sternum repair.

12 Claims, 3 Drawing Sheets

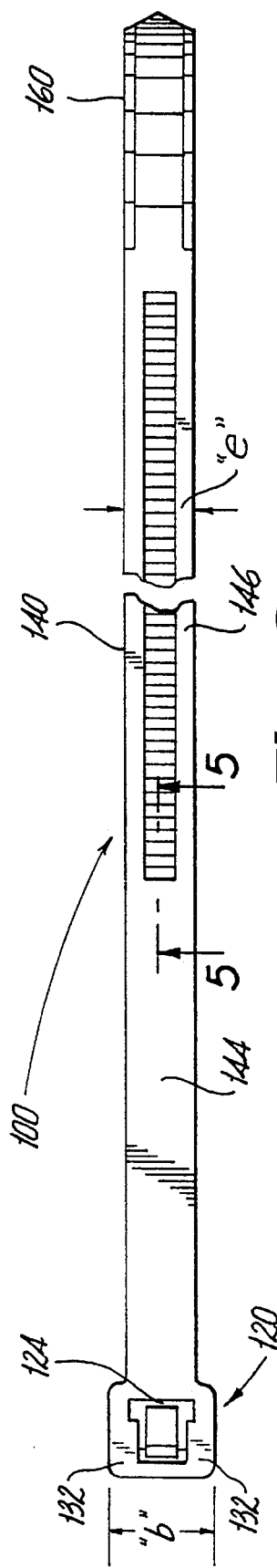
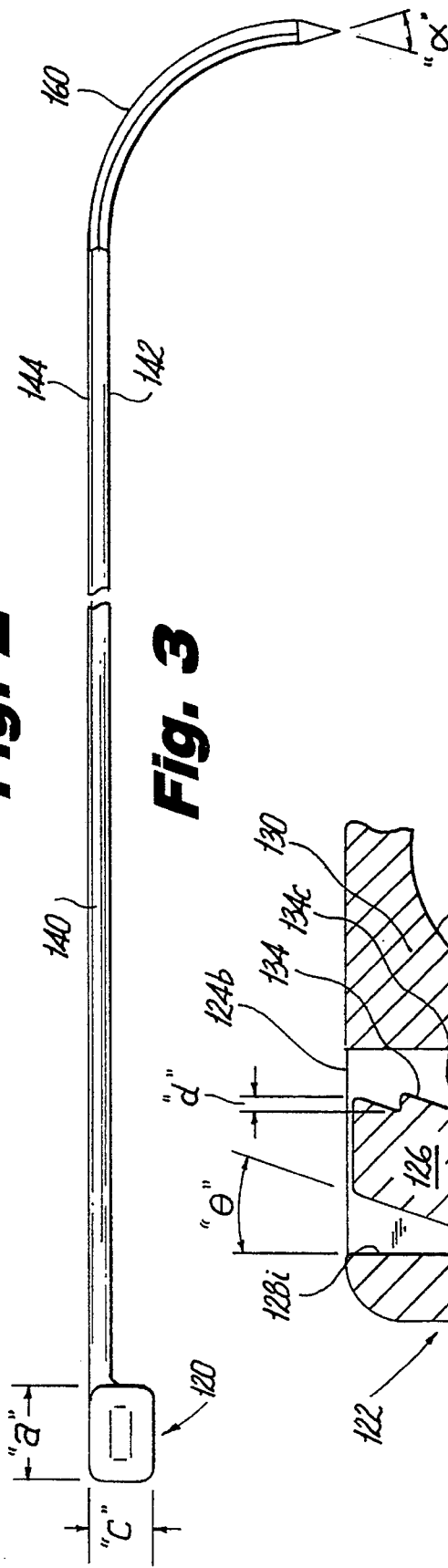
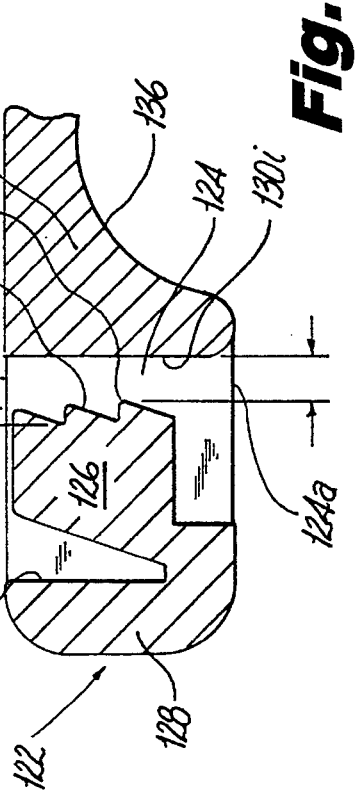
Fig. 2
Fig. 3
Fig. 4 ized
5,462,542

STERNUM BUCKLE WITH SERRATED STRAP

BACKGROUND OF THE INVENTION

1. Field of the Invention

The present invention relates to surgical devices for repair of split portions of tissue. In particular, the invention is directed to a strap assembly for securing a strap about split portions of a sternum to maintain the portions in adjacent contacting relation during healing.

2. Description of the Prior Art

During surgery that involves a median sternotomy, e.g., open heart surgery, the sternum is split longitudinally to permit access to the organs within the thoracic cavity. Upon completion of the surgery, the sternum is rejoined and closed securely. For proper healing to occur, the split sternum portions are preferably engaged in a face-to-face relationship and compressed together while the sternum heals.

Traditional methods for closing a sternum involve securing steel wires around or through the sternum halves and approximating the sternum by twisting the wires together.

Recently, a certain amount of emphasis has been directed towards the use of band or strap assemblies for sternum repair. Such assemblies typically include a locking mechanism which secures a strap in a closed looped configuration about the sternum portions. One example of an assembly of this type is described in U.S. Pat. No. 4,813,416 to Pollak et al. and includes a banding assembly having a curved surgical needle, an attached thin flat stainless steel band and a buckle mechanism. The sternum halves are brought to abutting closure by looping the band in position around or through the sternum portions and securing the band within the buckle mechanism.

Another example of a device contemplated for use in sternum closure is described in U.S. Pat. No. 4,730,615 to Sutherland. The Sutherland '615 device includes a head portion having a locking tang and a spine portion extending from the head portion. The spine portion is made of a biocompatible metal coated with a biocompatible polymer and possesses serrations along part of its length. In use, the spine portion is wrapped about the sternum and introduced within the head portion. The tang pierces the polymer coating and locks against a serration of the spine.

While utilization of steel wires and strap assemblies have been widely accepted for sternum repair, certain shortcomings with these devices are apparent. The use of steel wires presents problems to the surgeon during the operation and to the patient after closure is completed. Steel wires are difficult to maneuver and place around the sternum. The wire edges are often shard and can easily pierce through undesired areas including tissue surrounding the sternum area or the surgeon's gloves or fingers.

The strap assemblies known heretofore incorporate buckle mechanisms which are relatively structurally complex. For example, the buckle mechanism described in U.S. Pat. No. 4,813,416 includes a saddle part, interned flanges disposed on opposed sides of the saddle part and a loop segment. The saddle part and interned flanges define a band slide through course for reception of a portion of the band. A spring leaf extends upwardly from the loop segment through a slot in the saddle part. The rid end of the spring leaf is narrowed to define a spring tooth or projection which projects through an aperture formed in the band to maintain the closed band loop in a locked configuration.

Another significant disadvantage with the strap assemblies known heretofore is that the locking devices are typically made of a non bioabsorbable material such as stainless steel. The metallic components therefore remain within the patient indefinitely after healing has occurred.

Thus, there is a clear need for a surgical device which is simple in construction and effectively secures the divided sternum portions together for healing in a less invasive manner than that of known assemblies. It is also preferable that such device be at least partially fabricated from bioabsorbable materials. The present invention is directed to a bioabsorbable strap assembly of relatively simple construction, which securely retains a strap in a closed looped locking configuration around sternum portions to maintain the portions in adjacent engaged relation during healing.

SUMMARY OF THE INVENTION

Generally stated, the present invention is directed to a strap assembly for tissue repair. The strap assembly comprises a flexible elongated strap adapted to be looped about split portions of tissue and having a plurality of ratchet teeth along a portion thereof, and a buckle member attached to one end portion of the elongated strap. The buckle member comprises a base member defining a generally transverse channel dimensioned for reception of the elongated strap and a pawl member pivotally connected to the base member and within the transverse channel. The pawl member includes pawl teeth complementary in dimension and configuration to the ratchet teeth of the elongated strap and adapted to interlockingly engage the ratchet teeth to thereby secure the elongated strap in a looped tensioned condition about the tissue. The strap assembly has particular application in sternum repair. In the preferred embodiment, the buckle member and the strap member are integrally formed of a bioabsorbable material.

BRIEF DESCRIPTION OF THE DRAWINGS

The preferred embodiment of the present invention is described hereinabove with references to the drawings wherein:

FIG. 2 is a top plan view of the strap assembly of FIG. 1 illustrating the buckle and attached strap with a serrated portion;

FIG. 3 is a side plan view of the strap assembly of FIG. 1, illustrating a curved needle attached to the strap;

FIG. 4 is an enlarged cross-sectional view of the buckle, illustrating the base member and pawl member pivotally mounted within the base member;

DETAILED DESCRIPTION OF THE PREFERRED EMBODIMENT(S)

Figure 1:
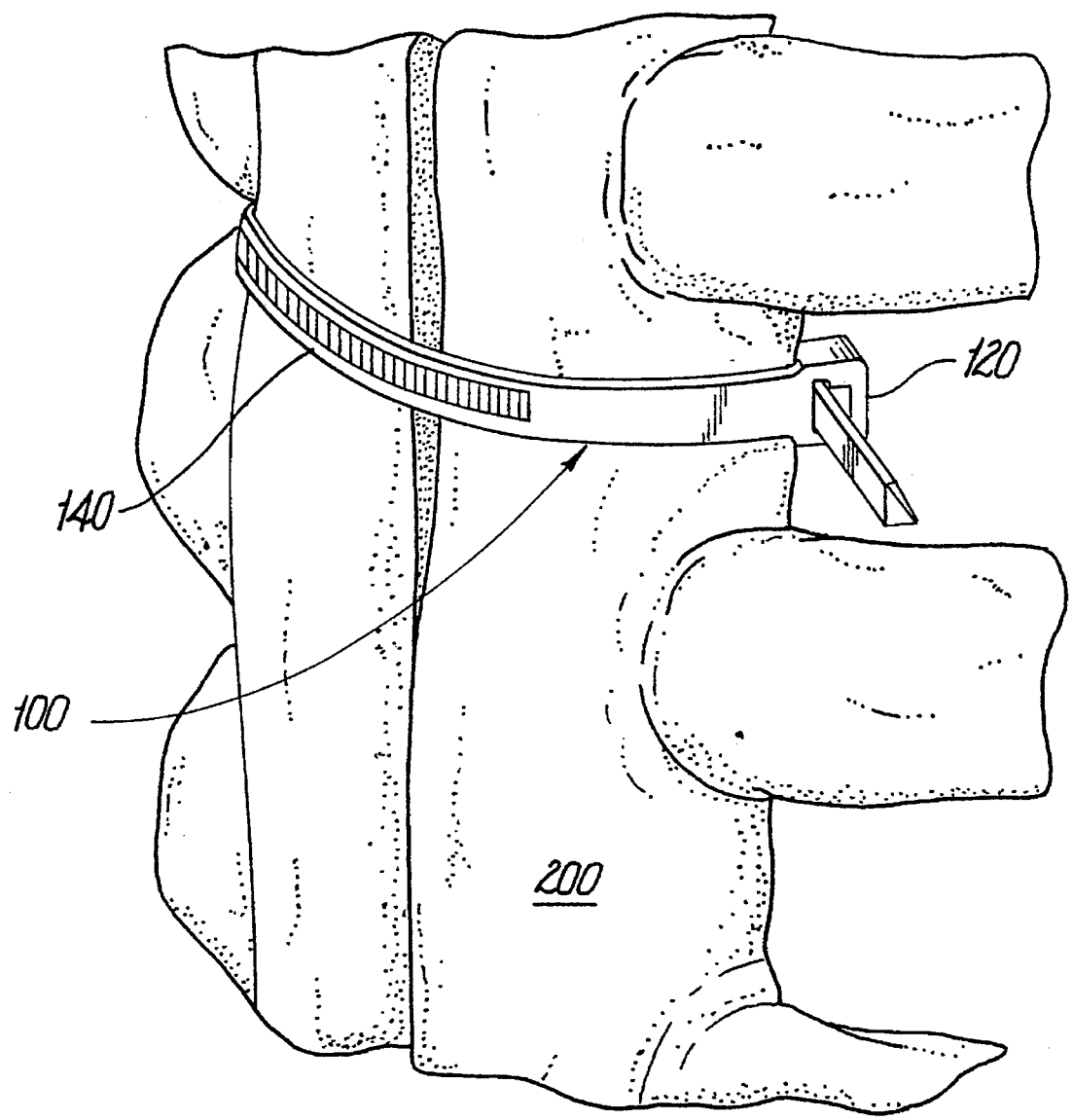
FIG. 1 is a perspective view of the strap assembly constructed in accordance with the principles of the present invention secured about a human sternum.

Referring initially to FIG. 1, there is illustrated in perspective view, a portion of a human sternum with the strap assembly of the present invention secured thereabout. Strap assembly 100 has particular application in the surgical repair of the sternum after, for example, a sternotomy. However, it is envisioned that strap assembly 100 may have other surgical applications as well. For example, strap assembly 100 may be used to ligate tissue such as a blood vessel or for attachment of bodily tissue portions other than the sternum.

Referring now to FIGS. 2–5, the novel operating components of strap assembly 100 will be discussed in detail. Strap assembly 100 includes buckle member 120, flexible elongated strap 140 integrally attached at one end portion thereof to the buckle member and needle 160 connected to the other end portion of the elongated strap. In the preferred embodiment, buckle member 120 and flexible elongated strap 140 are integrally formed by conventional molding techniques. Needle 160 is preferably attached to strap 140 by insert moulding the end of the strap about the needle, although other conventional attachment methods may be incorporated as well, or the needle 160 may be of the same moldable material as the strap, therefore on piece.

The preferred materials for buckle 120 and elongated strap 140 include synthetic bioabsorbable materials such as polymers or copolymers of glycolide, lactide, trimethylene carbonate, dioxanone, caprolactone or blends thereof. A suitable material for the components of strap assembly 100 is CAPRON® 8207F, a bioabsorbable material, which is manufactured by Allied Signal of Morris Plains, N.J. Other suitable materials for the components of strap assembly 100 include nonabsorbable materials such as. polycarbonate, polyester, polyethylene, polyamide, polypropylene, polytetrofluoroethylene (PTFE), polysulfone and acrylic.

Buckle 120 includes base member 122 having channel 124 extending therethrough generally transversely relative to strap 140 and pawl 126 pivotally mounted within the channel 124. Base member 122 includes first end wall 128 disposed away from strap 140 and second end wall 130 which is attached to the strap 140. Base member 122 also includes opposed side walls 132. These four walls 128, 130 and 132 encompass channel 124 which extends through base member 122 from an entry side 124a of the channel to an exit side 124b of the channel. First and second end walls 128, 130 define inner surfaces 128i, 130i. Inner surfaces 128i, 130i extend generally normal to the upper surface of buckle 120 and strap 140.

The length "a" (FIG. 3) of buckle 120 preferably ranges from about 0.265 inches to about 0.276 inches while the width "b" (FIG. 2) preferably ranges from about 0.275 inches to about 0.281 inches. The thickness or depth "c" (FIG. 3) of buckle 120 ranges from about 0.177 inches to about 0.183 inches.

Pawl 126 is integrally connected to the lower portion of first end wall 128 adjacent the entry side 124a of channel 124 and includes a plurality of pawl teeth 134 which face inner surface 130i of second wall 130. Pawl teeth 134 have crest portions 134c which lie in a common plane. This plane is in general parallel relationship with inner surface 130i of second wall 130. Pawl teeth 134 have a length ranging from about 0.039 inches to about 0.041 inches. The amplitude "d" (FIG. 4) of crest portions 134c range from about 0.013 inches to about 0.015 inches.

Pawl 126 defines an angle "O" with inner surface 128i of first end wall 128. The particular angular orientation of pawl 126 depends on several factors including the thickness of elongated strap 140 as well as the dimensions of the pawl. In the preferred embodiment, angle "O" ranges from about 15° to about 21°, with the preferred angle being about 18°. Pawl 126 is of sufficient rigidity to retain elongated strap 140 in a secured position, i.e., to prevent passage of the strap 140 in a negative loosening direction, while also possessing sufficient flexibility to permit passage of the strap 140 in a tightening direction during tensioning of the strap.

Referring particularly to FIGS. 3 and 4, the outer surface of second wall 130 of base member 122 has a generally arcuate portion 136. Arcuate portion 136 is strategically dimensioned to accommodate portions of the sternum bone when the buckle member is in the secured position of FIGS. 6 and 7. The radius of curvature of arcuate portion 136 ranges from about 0.085 inches to about 0.095 inches. Such curvature of arcuate portion 136 is advantageous because it reduces the likelihood of forming high stress areas where the buckle 120 and strap 140 meet. Thus, the curvature reduces the potential for a break to occur between buckle 120 and strap 140. Also, the curvature provides a more comfortable fit of the buckle 120 and strap 140 about the sternum.

Figure 5:
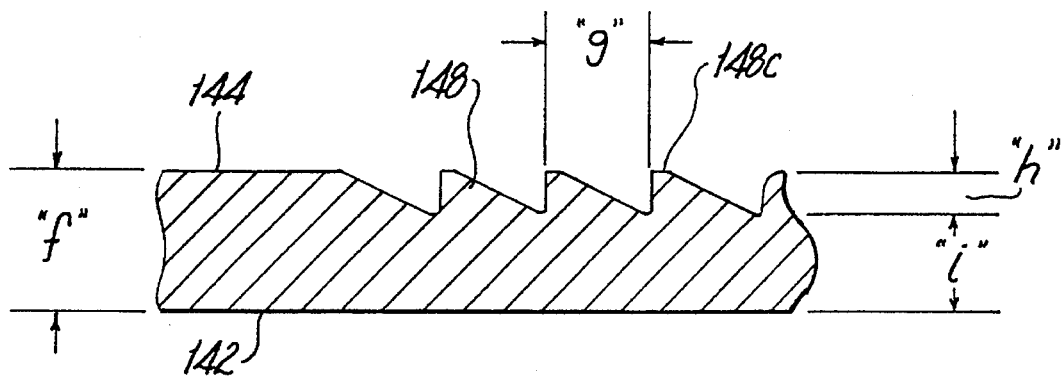
FIG. 5 is an enlarged cross-sectional view taken along the lines 5—5 of FIG. 2, illustrating the ratchet teeth of the serrated portion of the strap.
Figure 7:
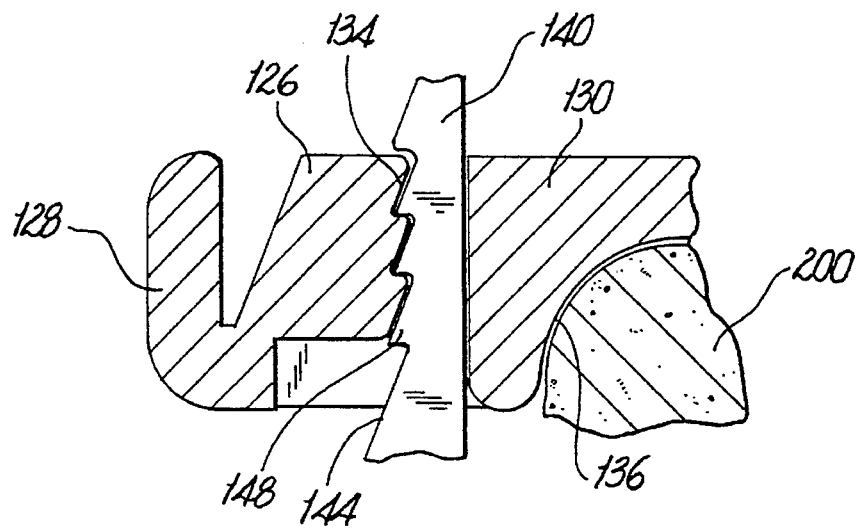
FIG. 7 is a cross-sectional view taken along lines 7—7 of FIG. 6, illustrating the secured condition of the buckle.

Referring now to FIGS. 2 and 5, elongated strap 140 will be discussed in detail. Strap 140 is approximately 12 inches in length, has a width "e" (FIG. 2) ranging from about 0.156 inches to about 0.160 inches and a thickness "f" (FIG. 5) ranging from about 0.048 inches to about 0.052 inches. Strap 140 defines inner and outer generally planar surfaces 142, 144. Outer surface 144 includes a serrated portion 146 having a plurality of ratchet teeth 148 (FIG. 7). Ratchet teeth 148 are complementary in dimension and configuration to pawl teeth 134 of pawl 126 so as to form a secure interlocking arrangement between strap 140 and the pawl 126. The length "g" of each pawl tooth ranges from about 0.039 inches to about 0.041 inches while the amplitude "h" of crest portions 148c of ratchet teeth 148 range from about 0.013 inches to about 0.014 inches. The thickness "i" of strap 140 at serrated portion 146 ranges from about 0.035 inches to about 0.037 inches which is less than the thickness of the remaining portion of the strap such that the crest portions 148c of ratchet teeth 148 lie in the same plane as the plane defined by the outer surface 144 of the strap 140. Accordingly, crest portions 148c of strap 140 do not extend beyond upper surface 144 of the strap, and, thus are minimally intrusive to the sternal tissue when the strap is secured about the sternum as will become appreciated from the description provided below.

Referring particularly to FIG. 3, needle 160 is attached to the free end portion of strap 140 by injection moulding or other conventional methods as previously mentioned. Needle 160 assists in penetrating the targeted parasternal location and positioning the strap 140 under the sternum and then outwardly at an opposite parasternal location. A curved surgical needle 160 is appropriate for sternum closure. The pointed end 162 of the needle defines an angle "a" of about 24°.

Further understanding of the strap assembly of the present invention will be realized from the description provided above of the use of same to secure split portions of a sternum together after surgery.

Figure 6:
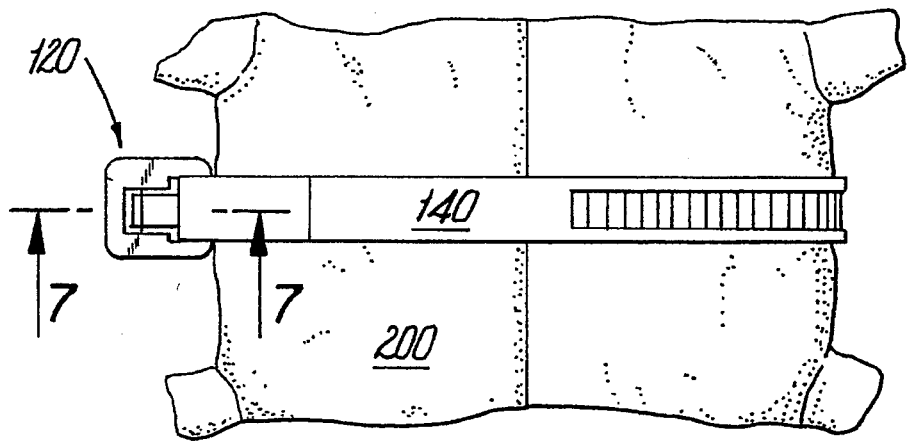
FIG. 6 is a plan view of the strap assembly in a looped tensioned condition about the sternum.

Referring now to FIG. 6, buckle 120 of strap assembly 100 is placed in a selected intercostal location at one side of the sternum 200. Needle 160 with attached elongated strap 140 is looped about the front side of sternum 200 and then inserted within intercostal space at the other side of the sternum where it is passed under both sternum halves 200 and exposed at the intercostal location adjacent buckle 120. Needle 160 with attached strap 140 is inserted into transverse channel 124 of base member 122 of buckle 120. In the alternative, needle 160 may be removed from strap 140 prior to insertion into transverse channel 124 if desired. Once through transverse opening 124, the surgeon grasps the strap end while holding buckle 120 with a surgical instrument, such as forceps or the like, and pulls the strap end in an outward tensioning direction to remove most of the slack formed in the loop.

At this point in the procedure, elongated strap 140 is not securely tightened about sternum portions 200. Preferably, one or more strap assemblies 100 are placed about selected locations of the sternum 200 in the same manner. When several strap assemblies 100 are in place around the sternum, each assembly may be tightened to a predetermined tension by grasping the free end of the strap and pulling the strap end until the sternum portions 200 are joined together in an adjacent face-to-face contacting relation.

As shown in the cross sectional view of FIG. 7, in the secured condition of assembly 100, pawl teeth 134 of pawl 126 interlockingly engage ratchet teeth 148 of strap 140. Thus, the complementary sets of ratchet and pawl teeth 134, 148 prevent strap 140 from loosening.

In the application of strap assembly 100 about sternum 200, outer surface 144 of elongated strap 140 faces away from the sternum 200. Accordingly, ratchet teeth 148 of strap 140 do not come into contact with sternum portions 200 and, thus, will not engage the sternal tissue to cause possible tearing or piercing of the sternal tissue. Further, since the serrated portion 146 is slightly recessed such that crest portions 148c of ratchet teeth 148 do not extend beyond upper surface 144 of the strap, the potential for the ratchet teeth to penetrate tissue within the thoracic cavity is also minimized.

As previously mentioned, arcuate outer surface portion 136 of base member 122 is strategically dimensioned to accommodate the curvature of the sternal bone as best shown in FIG. 7. Thus, in the secured condition of assembly 100, the gap between base member 122 of buckle 120 and the sternum 200 is minimized. Accordingly, the potential for strap assembly 100 to move about the sternum is minimized. Further, the positioning of pawl 126 on first end wall 128 facing second end wall 130 of buckle 120 biases the secured strap against sternum portions 200, thus, also minimizing the potential for a gap to form between strap 120 and the sternum portions.

The present invention provides a relatively simple and less traumatic means to effect sternum closure which can be performed rapidly and effectively by the surgeon. Since the buckle 120 and elongated strap 140 are made, in the preferred embodiment, entirely of bioabsorbable materials, the assembly may be left within the thoracic cavity without the need to open the cavity to remove the assembly after healing, which is sometimes required with conventional assemblies.

While the above description contains many specifics, these specifics should not be construed as limitations on the scope of the invention, but merely as an explanation of the preferred embodiment thereof. Those skilled in the art will envision many other possible variations that are within the scope and spirit of the invention as defined by the claims appended herein.

What is claimed is:

1. An assembly to be looped about split portions of tissue, which comprises:

a flexible elongated strap adapted to be looped about split portions of tissue, said strap including a plurality of ratchet teeth along a portion thereof;

a buckle member attached to one end portion of said elongated strap, said buckle member comprising:

a base member defining a generally transverse channel having an entrance end and an exit end, said channel dimensioned for reception of said elongated strap, said base member including first and second opposed end walls and a pair of opposed side walls; and a pawl member disposed within said transverse channel and being pivotally and integrally connected to an inner surface of said first end wall of said base member, said pawl member including pawl teeth complementary in dimension and configuration to said ratchet teeth of said elongated strap and adapted to interlockingly engage said ratchet teeth to thereby secure said elongated strap in a looped tensioned condition about the tissue, said pawl teeth of said pawl member facing an inner surface of said second end wall of said base member, said elongated strap being integral with an upper portion of said second end wall adjacent said exit end of said transverse channel of said base member, said elongated strap including at least an inner and outer surface, said inner surface of said elongated strap being in contact with the tissue portions when said strap is in said looped tensioned condition, said outer surface of said elongated strap including said portion of said elongated strap having said ratchet teeth.

2. The assembly according to claim 1, wherein said outer surface of said second end wall defines an arcuate portion dimensioned to accommodate a portion of human sternum tissue when said buckle member is in a secured position.

3. The assembly according to claim 2, wherein said arcuate portion of said outer surface of said second end wall defines a radius of curvature ranging from about 0.80 inches to about 1.10 inches.

4. The assembly according to claim 1, wherein said base member includes lower and upper surfaces, and wherein said outer surface of said elongated strap integral with said base member lies in the same plane defined by said upper surface of said base member.

5. The assembly according to claim 1, wherein said ratchet teeth of said portion of said elongated strap defines crest portions which lie in the same plane defined by said outer surface of said elongated strap.

6. The assembly according to claim 1, wherein said inner surface of said second end wall extends generally transverse relative to said elongated strap.

7. The assembly according to claim 6, wherein said pawl teeth of said pawl include crest portions which lie in a common plane generally parallel to a plane defined by said inner surface of said second wall of said base member.

8. The assembly according to claim 7, wherein said pawl member and said inner surface of said first end wall define an angle ranging from about 15° to about 21°.

9. The assembly according to claim 1, wherein a surgical needle is attached to the other end portion of said elongated strap.

10. The assembly according to claim 1, wherein said elongated strap and said buckle member and needle are integrally molded to form a single piece unit.

11. The assembly according to claim 1, wherein said elongated strap and said buckle member are integrally formed and comprise a bioabsorbable material selected from the group consisting of polymers or copolymers of glycolide, lactide, trimethylene carbonate, lactone, dioxanone and caprolactone.

12. The assembly according to claim 1, wherein said elongated strap and said buckle member are integrally formed and comprise a nonabsorbable material selected from the group consisting of polycarbonate, polyethylene, polypropylene, polyvinyl chloride, polytetrafluoroethylene and acrylic.

* * * * *